(12) United States Patent
Tamaki

(10) Patent No.: US 6,875,226 B2
(45) Date of Patent: Apr. 5, 2005

(54) LASER THERAPY APPARATUS AND LASER THERAPY

(76) Inventor: Hideshi Tamaki, 1-39-1 Kami-Ishihara, Chofu, Tokyo (JP) 1820035

( * ) Notice: Subject to any disclaimer, the term of this patent is extended or adjusted under 35 U.S.C. 154(b) by 0 days.

(21) Appl. No.: 10/621,169

(22) Filed: Jul. 16, 2003

(65) Prior Publication Data

US 2005/0015078 A1   Jan. 20, 2005

(51) Int. Cl.$^7$ .................................. A61N 5/067
(52) U.S. Cl. ........................... 607/89; 385/128
(58) Field of Search .............. 65/385; 601/15; 606/2, 606/13, 16; 607/89; 385/128

(56) References Cited

U.S. PATENT DOCUMENTS

| | | | | |
|---|---|---|---|---|
| 4,473,599 A | * | 9/1984 | Elion | ........................... 65/423 |
| 6,487,879 B1 | * | 12/2002 | Blackwell et al. | ............. 65/414 |
| 2003/0214987 A1 | * | 11/2003 | Yamanaka et al. | ............ 372/43 |

FOREIGN PATENT DOCUMENTS

| | | |
|---|---|---|
| JP | H05-032516 | 2/1993 |
| JP | H09-175923 | 7/1997 |
| JP | 2002/202418 | 7/2002 |

* cited by examiner

*Primary Examiner*—Roy D Gibson
*Assistant Examiner*—Henry M Johnson, III
(74) *Attorney, Agent, or Firm*—Cowan, Liebowitz & Latman, P.C.; Mark Montague

(57) ABSTRACT

An optical therapy device has an optical fiber having a coaxial structure including at least a core to be provided as a center thereof, a clad that covers the outer periphery of the core, and a protective layer that covers the outer periphery of the clad. At a tip portion of the optical fiber, a part of the protective layer is removed to expose the clad. The optical fiber is arranged on the tip of the laser therapy apparatus. Furthermore, the tip portion of the optical fiber is brought into contact with a titanium compound, or the titanium compound is applied on an affected part of a patient, followed by irradiating a laser beam on the affected part.

16 Claims, 1 Drawing Sheet

LASER THERAPY APPARATUS AND LASER THERAPY

BACKGROUND OF THE INVENTION

1. Field of the Invention

The present invention relates to a laser therapy apparatus suitable for prevention and treatment of a dental disease such as periodontosis or alveolar pyorrhea, and also for prevention and treatment of a skin disease. The present invention also relates to a laser therapy method suitable for prevention and treatment of a dental disease such as periodontosis or alveolar pyorrhea, and also for treatment of a skin disease.

2. Description of the Related Art

In periodontosis and alveolar pyorrhea, gums are invaded by bacteria being accumulated in dental plaque, and inflammation of the gum occurs. Furthermore, the inflammation progresses to depths of a dental-surrounding tissues and a crevice called a periodontal pocket is made. In recent years, laser beam irradiation on the affected part of a tooth has been conducted for the treatment in the mouth or oral cavity, such as incision, hemostasis, and anti-inflammation, dental caries prevention, and removal of tartar/dental plaque. In this case, a medical laser apparatus having a laser beam generator in the main body of an irradiation probe has been used.

However, a laser beam applies to the conventional dentistry to surgically deal with inflammation region and a periodontal pocket of the gums invaded with bacteria, as mentioned above, rather than a direct treatment for periodontosis, alveolar pyorrhea and the like.

On the other hand, as a technique in which titanium oxide is applied on the dental therapy, for example, the following one has been proposed. That is, in the technique, a photocatalyst material such as titanium dioxide having oxidizability with irradiation of light is arranged so as to be brought into contact with a tooth or cover a tooth, so that dental plaque, which is the cause of dental caries or periodontal disease, is broken down. Thus, the technology prevents these diseases. For detailed explanation, in the technology, a liquefied material prepared as a mixture of powdered titanium dioxide and rubber-based polymer resin is applied to coat the tooth on treatment. As a light-emitting material, a phosphorescent material is proposed in. For example, see Japanese Laid-Open specification Heisei09-175923.

In addition, there is proposed a technology to prevent the dental caries and the periodontal disease and prevent the generation of offensive odor, in which a hardened material that contains metal-carrying titania fine powders is irradiated appropriately with visible light to sterilize the hardened material and peripheral tooth region. For example, see Japanese Laid-Open specification Heisei05-32516.

However, these technologies are just prevention technologies for periodontal disease, that is, these are not practical therapeutic technologies for periodontal disease and alveolar pyorrhoea.

SUMMARY AND OBJECT OF THE INVENTION

The present invention has been completed in consideration of the above circumstances. An object of the present invention is to provide a laser therapy apparatus suitable for the prevention and treatment of a dental disease such as periodontosis or alveolar pyorrhea, and also for the prevention and treatment of a skin disease.

The inventor has dedicated to making diligent studies and finally found out that the above problem can be solved by attaching a titanium compound on the tip portion of an optical fiber of a laser therapy apparatus using a laser beam.

In a first aspect of the invention, an optical fiber for a laser therapy apparatus comprises: a core which is provided as a center of the optical fiber; a clad which is coaxial with the core and covers the outside of the core; a protective layer that is coaxial with the core and the clad, and covers the outside of the clad to expose a tip-side surface of the clad; and a titanium compound to be attached on a tip portion of the optical fiber.

In a second aspect of the invention, a laser therapy apparatus has an optical source that emits a laser beam and a light-guiding part for irradiating the laser beam to a target area to be treated, in which at least a tip portion of the light-guiding part is formed of an optical fiber, and the optical fiber comprises: a core which is provided as a center of the optical fiber; a clad which is coaxial with the core and covers the outside of the core; a protective layer that is coaxial with the core and the clad, and covers the outside of the clad to expose a tip-side surface of the clad; and a titanium compound to be attached on a tip portion of the optical fiber.

In a third aspect of the present invention, a laser therapy apparatus is prepared by removing a protective layer on the tip portion of the optical fiber to expose the side surface of a clad, bringing the tip portion of the optical fiber into contact with a titanium compound, and attaching the titanium compound on the tip portion of the optical fiber by a laser beam radiation from the optical fiber.

In a fourth aspect of the present invention, a laser therapy method comprises the steps of: removing a protective layer on the tip portion of the optical fiber having a core, clad, and a protective layer to expose the side surface of a clad; bring the tip portion of the optical fiber into contact with a titanium compound; attaching the titanium compound on the tip portion of the optical fiber by a laser beam radiation from the optical fiber; bringing the tip portion of the optical fiber on which the titanium compound is being attached into contact with a target area to be treated; and irradiating a laser beam to the target area to be treated through the optical fiber.

In a fifth aspect of the present invention, a laser therapy method, comprises the steps of: bringing a tip portion of an optical fiber having a core, a clad, and a protective layer, where the side surface of the clad is being exposed by removing the protective layer and a titanium compound is attached, into contact with a target area to be treated; and irradiating a laser beam to the target area to be treated through the optical fiber.

In a sixth aspect of the present invention, a laser therapy method comprises the steps of: applying a titanium compound on a target to be treated; bringing a tip portion of an optical fiber having a core, a clad, and a protective layer, where the side surface of the clad is being exposed by removing the protective layer, into contact with the target area to be treated; and irradiating a laser beam to the target area to be treated through the optical fiber.

Preferably, the titanium compound attaches on the tip portion of the optical fiber by the laser beam after contacting the tip portion of the optical fiber with a titanium oxide powder.

Preferably, furthermore, the titanium compound may be attached on at least an exposed portion of the clad.

Preferably, furthermore, titanium oxide may be used as the titanium compound.

Preferably, furthermore, the optical fiber may be detachable from the light-guiding part.

Preferably, furthermore, the optical fiber is a quartz fiber.

It seems that at the time of bringing the tip portion of an optical fiber into titanium oxide powder and emitting a laser beam, a substance is generated by a contact reaction between a laser beam and titanium oxide attached through cracks of the clad created by intense energy of the laser beam, and the substance may play a key role for an effective treatment. It seems that by this reaction, a titanium oxide including at least a low valence titanium oxide may be generated.

BRIEF DESCRIPTION OF THE DRAWINGS

The following detailed description, given by way of example and not intended to limit the present invention solely thereto, will best be appreciated in conjunction with the accompanying drawings, wherein like reference numerals denote like elements and parts, in which.

DETAILED DESCRIPTION OF THE INVENTION

Embodiment 1

Figure 1:
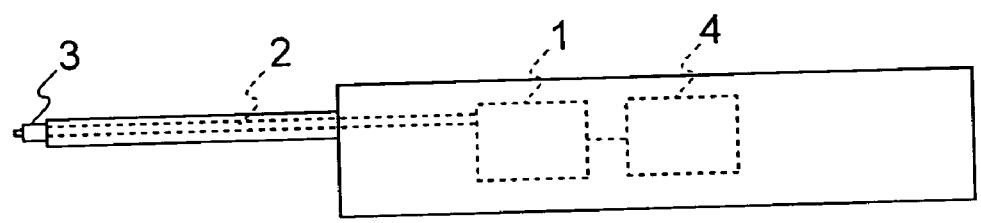
FIG. 1 is a schematic side view that illustrates the configuration of a laser therapy apparatus in accordance with Embodiment 1 of the present invention.

Referring to the drawings, FIG. 1 is a schematic diagram for illustrating the configuration of a laser therapy apparatus as Embodiment 1. The laser therapy apparatus comprises an optical source 1 for emitting a laser beam and a light-guiding part 2 for irradiating a laser beam to a target area to be treated. In addition, at least a laser-beam radiation part of a tip portion of the light-guiding part 2 is formed of a specific optical fiber 3 described later.

A control part 4 of the laser therapy apparatus is responsible for switching the optical source 1 on and off and opening and closing the light-guiding part 2 from the optical source 1 to the laser-beam radiation part. In the control part 4, it is preferable to equip a timer or a switch for setting an irradiation time of the laser beam. The present laser therapy apparatus may be provided by reconstructing a commercially-available laser therapy apparatus. For instance, such an apparatus may be "CONTACLASE" (Registered trademark) (manufactured by SLT Japan Co., Ltd.).

Furthermore, the optical source 1 is not limited to a specific one, and any kind of visible light laser, infrared laser, and so on may be suitable. For instance, the allowable lasers include a Nd-YAG laser, a ruby laser, a Nd glass laser, a LD-YAG laser, and an Er-YAG laser and the like. Among them, a Nd-YAG laser is preferable.

The light-guiding part 2 is responsible for guiding a light beam from the optical source 1 to an optical fiber 3 which is a laser-beam radiation part equipped on the tip portion. In addition, at least a tip portion of the laser-beam radiation part is formed of an optical fiber 3.

Figure 2:
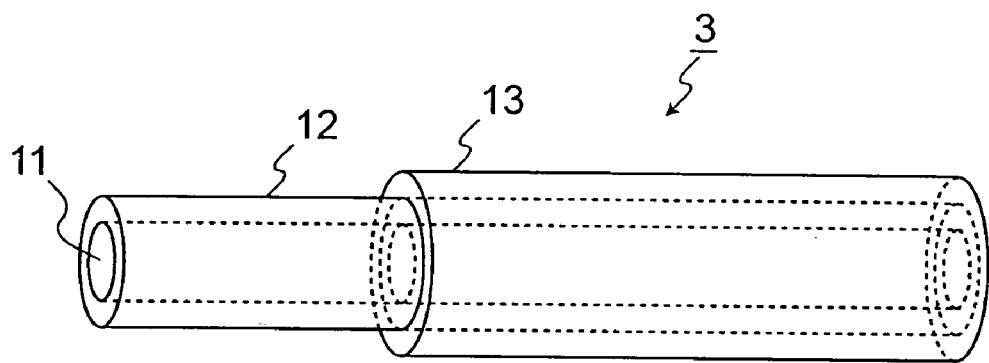
FIG. 2 is a schematic perspective view that illustrates the configuration of an optical fiber to be used in the laser therapy apparatus in accordance with Embodiment 1 of the present invention.

FIG. 2 is a diagram that illustrates the optical fiber 3 to be used in the laser therapy apparatus in accordance with Embodiment 1 of the present invention. The optical fiber 3 is constructed as a coaxial structure comprising at least a core 11 provided as a center thereof, a clad 12 that covers the outer periphery of the core 11, and a protective layer 13 that covers the outer periphery of the clad 12. Furthermore, as shown in FIG. 2, a part of the protective layer is removed to expose the side surface of the clad 12 at tip portion of the optical fiber 3.

The optical fiber 3 may be preferably provided as a quartz optical fiber. Alternatively, a zirconium fluorine glass fiber or the like may be used.

The diameter of the optical fiber 3 may be, but not limited to, preferably 1.5 mm or less, more preferably 1.0 mm or less.

The length of the optical fiber 3 may be, but not limited to, preferably 5 mm or more protruded from the tip of a hand piece when it is clinically applied using the hand piece in consideration of contacting with the periodontal pocket of a patient.

The shape of the optical fiber 3 may be straight as shown in FIG. 2. Alternatively, however, an operator of the apparatus may manipulate easily when the laser-beam radiation part is curved.

Furthermore, the optical fiber 3 is preferably disposable from a hygienically point of view, due to saliva or the like on the fiber 3 after a treatment.

Therefore, it is preferable to construct the tip portion so as to be easily cut off with a fiber cutter such as a sapphire knife, or removably arranged in the apparatus. Here, for these means, any conventional means well-known in the art can be used.

On the tip portion of the optical fiber 3, the protective layer 13 is removed and a side curved surface of the clad 12 is exposed. In addition, the tip portion of the optical fiber 3 is attached with a titanium compound not shown in the figure. The titanium compound needs to be attached on at least the clad 12 of the optical fiber 3. The removal of the protective layer 13 is effectively attained by burning off with fire of a lighter, which is operationally preferable.

As a method for attaching the titanium compound on the tip portion of the optical fiber 3, there is a simple and most effective method in which the clad 12 is exposed by peeling off the protective layer 13 of the tip portion of the optical fiber 3 and the tip portion of the optical fiber 12 is then brought into contact with titanium oxide powders, followed by irradiating a laser beam. Using such a method, the titanium compound can be attached on the tip portion of the optical fiber 3, and finally the laser therapy apparatus of the present embodiment can be obtained.

Titanium oxide to be used in the case may be either of rutile-type or anatase-type. An average particle size of titanium is preferably 10 $\mu$m or less, more preferably 5 $\mu$m or less.

Next, a method for performing a laser therapy using a laser therapy apparatus of the present embodiment 1 will be described.

At first, in the tip portion of the optical fiber 3 which constitutes the tip portion of the laser therapy apparatus, the operator peels off the protective layer 13 to expose the side surface of the clad 12.

Then, the operator brings the exposed portion into contact with titanium oxide powders, followed by irradiating a laser beam to attach the titanium oxide at least on the surface of the clad 12.

Consequently, by the operation of the operator at the time of a treatment, the laser beam is allowed to be irradiated to the titanium compound such that the titanium compound attaches on the tip portion of the optical fiber 3.

Subsequently, the optical fiber 3 provided as a laser-beam radiation part is brought into contact with an affected part or very close to the affected part, followed by directly irradiating a laser beam on the affected portion.

In the case of a periodontal disease, the tip of the optical fiber 3 is directly inserted into a periodontal pocket and then a laser beam is directly irradiated thereon to treat the periodontal disease.

Hereinafter, a concrete example of the treatment method will be explained in detail.

CONCRETE EXAMPLE 1

A commercially-available laser therapy apparatus having a Nd-YAG laser (1.06 μm in wavelength), "CONTACLASE (registered trademark)" (manufactured by SLT Japan Co., Ltd.) was modified and used. The protective layer of the tip portion of an optical fiber equipped with a light-guiding part of the apparatus is burnt with fire of the lighter to expose the clad, followed by inserting the tip portion of the optical fiber into titanium oxide powders in a 25-ml bottle.

Next, the laser beam is irradiated to attach the titanium oxide on the tip portion by irradiating a laser beam at a power of 500 mJ, 10 pps. Furthermore, the inventor confirms that the titanium compound such as titanium oxide is attached on the tip portion of the optical fiber by a phase contrast microscope.

Using this apparatus, when a laser therapy is conducted on a patient A suffered from the periodontal disease by irradiating a laser beam, the periodontal disease is completely cured such that the generation of pus is stopped and the teeth becomes stable without shaking. After that, there is no recurrence, and the patient A is not troubled afterwards by many symptoms of periodontal disease.

CONCRETE EXAMPLE 2

Just as in the case with Concrete Example 1, a treatment is performed on a patient B who is suffering from the periodontal disease. In the case of the patient B, the treatment is performed every one time per about two weeks. As a result, after 30 days from the initiation of the treatment (i.e., the patient was treated 3 times), swelling and pain are disappeared, the generation of pus is stopped, and the shaky teeth become stable in place.

Embodiment 2

In a laser treatment method of Embodiment 2 of the present invention, a titanium compound is applied on an affected part directly, and then the tip of the laser therapy apparatus is brought into contact with the affected portion, while allowing an irradiation of a laser beam. Therefore, the emission of a laser beam at the time of a treatment allows the tip portion of the laser therapy apparatus to be attached on the titanium compound. In this case, the titanium compound may be in the form of milky liquid, paste, a water solution, or the like, and the milky liquid, paste, a water solution, or the like is applied on the affected portion.

Furthermore, each of the above embodiments is one of preferred embodiments of the present invention. However, the invention is not limited to these embodiments. Within the gist of the present invention, various kind of modifications and variations may be allowed.

Furthermore, in each of the above embodiments, a laser therapy apparatus and a laser therapy method of the present invention are applied to dental diseases. However, the present invention is not limited to such an application. It is also applicable to dermatological diseases.

According to the present invention, therefore, a laser therapy apparatus of the present invention is suitable for the prevention and treatment of dental diseases such as periodontal disease and alveolar pyorrhea, and is also suitable for the prevention and treatment of dermatological diseases.

What is claimed is:

1. An optical fiber for a laser therapy apparatus, comprising:
    a core which is provided as a center of the optical fiber;
    a clad which is coaxial with the core and covers the outside of the core;
    a protective layer that is coaxial with the core and the clad, the protective layer partially covering the outside of the clad to expose a tip-side surface of the clad; and
    a titanium compound to be attached on a tip portion of the optical fiber.

2. An optical fiber as claimed in claim 1, wherein the optical fiber is a quartz fiber.

3. An optical fiber as claimed in claim 1, wherein the titanium compound attaches on at least exposed portion of the clad.

4. An optical fiber as claimed in claim 1, wherein the titanium compound is titanium oxide.

5. A laser therapy apparatus comprising:
    an optical source that emits a laser beam; and
    a light-guiding part for irradiating the laser beam to a target area to be treated, in which at least a tip portion of the light-guiding part is formed of an optical fiber, the optical fiber comprises:
    a core which is provided as a center of the optical fiber;
    a clad which is coaxial with the core and covers the outside of the core;
    a protective layer that is coaxial with the core and the clad, the protective layer partially covering the outside of the clad to expose a tip-side surface of the clad; and
    a titanium compound to be attached on a tip portion of the optical fiber.

6. A laser therapy apparatus as claimed in claim 5, wherein the titanium compound attaches on the tip portion of the optical fiber by a laser beam after contacting the tip portion of the optical fiber with titanium oxide powders.

7. A laser therapy apparatus as claimed in claim 5, wherein the optical fiber is a quartz fiber.

8. A laser therapy apparatus as claimed in claim 5, wherein the titanium compound attaches on at least exposed portion of the clad.

9. A laser therapy apparatus as claimed in claim 5, wherein the titanium compound is titanium oxide.

10. A laser therapy apparatus as claimed in claim 5, wherein the optical fiber is detachable from the light-guiding part.

11. A laser therapy apparatus, comprising:
    an optical source for emitting a laser beam and a light-guiding part for irradiating the laser beam to a target area to be treated, where at least a tip portion of the light-guiding part is formed of an optical fiber,
    a protective layer on a tip portion of the optical fiber partially removed to expose a side surface of a clad,
    the tip portion of the optical fiber in contact with a titanium compound, and
    the titanium compound is attached on the tip portion of the optical fiber by a laser beam radiation from the optical fiber.

12. A laser therapy apparatus as claimed in claim 11, wherein the titanium compound attaches on the tip portion of the optical fiber by the laser beam after contacting the tip portion of the optical fiber with titanium oxide powders.

13. A laser therapy apparatus as claimed in claim 11, wherein the optical fiber is a quartz fiber.

14. A laser therapy apparatus as claimed in claim 11, wherein the titanium compound is attached on at least exposed portion of the clad.

15. A laser therapy apparatus as claimed in claim 11, wherein the titanium compound is titanium oxide.

16. A laser therapy apparatus as claimed in claim 11, wherein the optical fiber is detachable from the light-guiding part.

* * * * *